United States Patent
Hietala

(10) Patent No.: US 11,448,640 B2
(45) Date of Patent: Sep. 20, 2022

(54) RESPIRATORY GAS SENSOR SYSTEM WITH COLOR DETECTION

(71) Applicant: GE Precision Healthcare LLC, Wauwatosa, WI (US)

(72) Inventor: Mika Harri Juhani Hietala, Espoo (FI)

(73) Assignee: GE Precision Healthcare LLC, Wauwatosa, WI (US)

( * ) Notice: Subject to any disclaimer, the term of this patent is extended or adjusted under 35 U.S.C. 154(b) by 274 days.

(21) Appl. No.: 16/653,177

(22) Filed: Oct. 15, 2019

(65) Prior Publication Data
US 2021/0109084 A1    Apr. 15, 2021

(51) Int. Cl.
| | | |
|---|---|---|
| G01N 33/497 | (2006.01) | |
| A61M 39/10 | (2006.01) | |
| G01N 21/3504 | (2014.01) | |
| G08B 5/36 | (2006.01) | |

(52) U.S. Cl.
CPC ........... *G01N 33/497* (2013.01); *A61M 39/10* (2013.01); *G01N 21/3504* (2013.01); *G08B 5/36* (2013.01); *A61M 2039/1005* (2013.01)

(58) Field of Classification Search
CPC . G01N 33/497; G01N 21/3504; A61M 39/10; A61M 2039/1005; A61M 16/085; A61M 2230/43; A61M 2230/432; G08B 5/36; A61B 5/08; A61B 5/082; A61B 5/083; A61B 5/0833; A61B 5/0836; A61B 5/087; A61B 5/097
See application file for complete search history.

(56) References Cited

U.S. PATENT DOCUMENTS

| | | | |
|---|---|---|---|
| 8,642,966 B2 | 2/2014 | Weckstrom et al. | |
| 2002/0103444 A1* | 8/2002 | Ricciardelli | G01F 1/46 600/532 |
| 2008/0041172 A1* | 2/2008 | Jaffe | G01N 1/24 73/863.83 |
| 2010/0168599 A1* | 7/2010 | Esposito | A61M 16/0816 600/532 |
| 2015/0126872 A1* | 5/2015 | Dubielczyk | A61B 5/0077 600/473 |
| 2016/0245830 A1* | 8/2016 | Mace | G16H 40/40 |
| 2017/0086677 A1 | 3/2017 | Pekander et al. | |
| 2019/0117930 A1* | 4/2019 | Al-Ali | A61B 5/0836 |

* cited by examiner

*Primary Examiner* — Orlando Bousono
(74) *Attorney, Agent, or Firm* — Andrus Intellectual Property Law, LLP

(57) ABSTRACT

A gas analyzer for measuring a respiratory gas component includes an emitter that transmits infrared (IR) radiation through a measurement chamber containing respiration gas, and at least one IR detector configured to receive at least a portion of the IR radiation transmitted through the measurement chamber and to generate radiation measurement data based on the received IR radiation. A light source is configured to emit light onto a color indicator, wherein the color indicator is one of a predefined set of colors. A color detector is configured to detect light reflected by a color indicator so as to identify color information. The controllers configured to determine a respiratory gas component concentration within the measurement chamber based on the color information and the radiation measurement data.

20 Claims, 7 Drawing Sheets

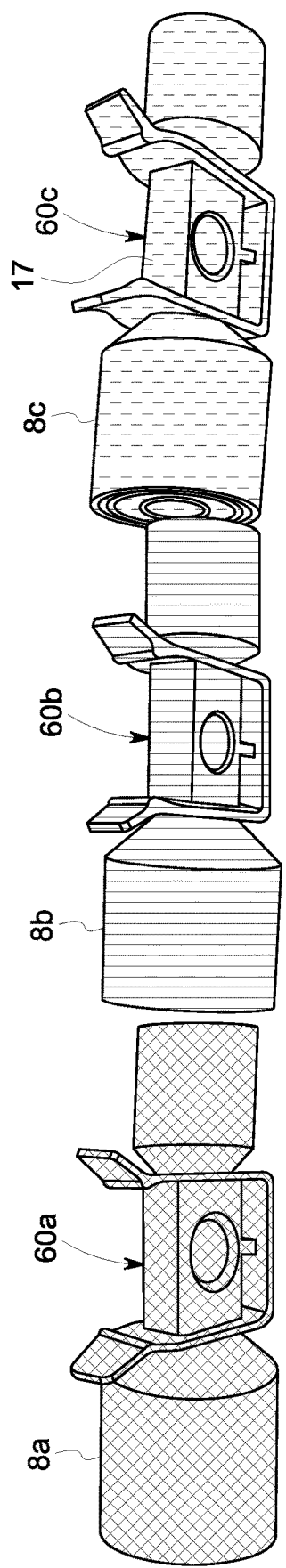
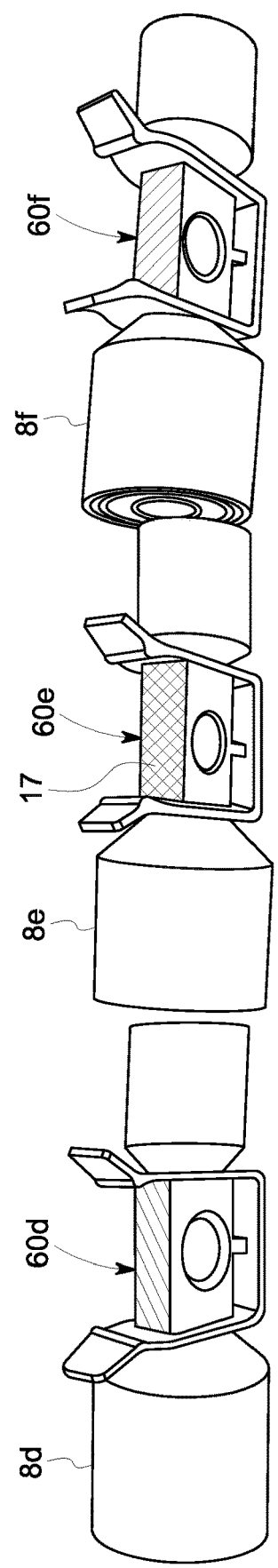
FIG. 5A
FIG. 5B

RESPIRATORY GAS SENSOR SYSTEM WITH COLOR DETECTION

BACKGROUND

The present disclosure generally relates to respiratory gas sensor systems that measure one or more respiratory gas components in a breathing circuit of a patient, and more particularly to respiratory sensor systems having a gas analyzer that includes color detection systems for component identification.

In anesthesia and in intensive care, the condition of a patient is often monitored by analyzing the gas inhaled and exhaled by the patient for its content. For this reason, either a small portion of the respiratory gas is delivered to a gas analyzer or the gas analyzer is directly connected to the respiratory circuit. In a non-dispersive infrared (NDIR) gas analyzer, the measurement is based on the absorption of infrared (IR) radiation in the gas sample. A radiation source directs a beam of infrared radiation through a measuring chamber to a radiation detector whose output signal depends on the strength of the absorption of the radiation in the sample gas.

The radiation source typically comprises an electrically heated filament or surface area and radiation collecting optics and emits radiation within a spectral region. The gas sample to be analyzed, i.e. the sample gas, is fed through the measuring chamber, whereupon the gas mixture is included in the chamber for analysis. The measuring chamber can be a tubular space, for example, with inlet and outlet for the sample gas and provided with windows that are transparent at the measurement IR wavelength and permit transmission of the IR wavelength through the chamber. Radiation is absorbed by the gas sample when passing through the measuring chamber, and thus the amount of the measurement IR wavelength that is transmitted through the chamber (i.e., from one window to the other) is indicative of certain gas component amount(s) in the gas sample.

The radiation detector generates an electrical signal that depends on the radiation power falling on its sensitive area. The detector type in a gas analyzer depends on its measurement wavelength. For measurement within a broad spectral range, a thermal detector is convenient because its sensitivity only depends on the efficiency of the conversion of radiation to heat. To make the detector's output signal sensitive to a certain gas component, the wavelength band of the radiation coming to the detector is selected so that the gas component absorbs radiation within it. This selection is made using an optical bandpass filter whose bandwidth may be, for example, 1%-2% of the center wavelength.

Gas analyzers can be configured to measure different gas components. The absorption of the gas sample is measured at a wavelength band selected to match the absorption spectra of the gas component(s) of interest. Measurement of more than one gas component can be accomplished by using one radiation detector and by changing the optical bandpass filters on the optical path in succession. It is also possible to use several radiation detectors, combined with corresponding bandpass filters. Different respiratory gases have widely spaced wavelength regions of absorption. Carbon dioxide and nitrous oxide can be measured between 3900 nm and 4600 nm whereas anesthetic agents absorb in the 8000 nm to 10000 nm region.

To measure the strength of absorption, it is necessary to know the zero levels of the analyzer at the measured wavelength(s). The zero level is the detector signal obtained at a wavelength when the sample gas does not absorb IR radiation at that wavelength. The strength of absorption is calculated by forming the ratio between the zero level signal and the detector signal, supposing that absence of radiation results in a zero or otherwise known signal. It is possible to update the zero levels by separately measuring zero gas that is known to not absorb radiation at the measurement wavelengths. This method is commonly used in a sidestream configuration, for example, where a gas sample is drawn from the respiratory circuit and analyzed separately.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

In one embodiment, a gas analyzer for measuring a respiratory gas component includes an emitter that transmits infrared (IR) radiation through a measurement chamber containing respiration gas, and at least one IR detector configured to receive at least a portion of the IR radiation transmitted through the measurement chamber and to generate radiation measurement data based on the received IR radiation. A light source is configured to emit light onto a color indicator, wherein the color indicator is one of a predefined set of colors. A color detector is configured to detect light reflected by a color indicator so as to identify color information. The controllers configured to determine a respiratory gas component concentration within the measurement chamber based on the color information and the radiation measurement data.

A respiratory gas sensor system for measuring a respiratory gas component includes an airway adapter providing a measurement chamber for respiratory gases, wherein the airway adapter includes a color indicator, and a gas analyzer configured to fit with the airway adapter and measure a respiratory gas component concentration in the measurement chamber. The gas analyzer includes a light source configured to emit light onto the color indicator and a color detector configured to detect light reflected by the color indicator so as to identify color information based thereon. A controller is configured to automatically identify a zero-point value based on the color information, and then to determine the respiratory gas concentration utilizing the zero-point value.

Various other features, objects, and advantages of the invention will be made apparent from the following description taken together with the drawings.

BRIEF DESCRIPTION OF THE DRAWINGS

The present disclosure is described with reference to the following Figures.

FIGS. 5A and 5B depict airway adapters having color indicators according to embodiments of the disclosure.

DETAILED DESCRIPTION

Figure 1:
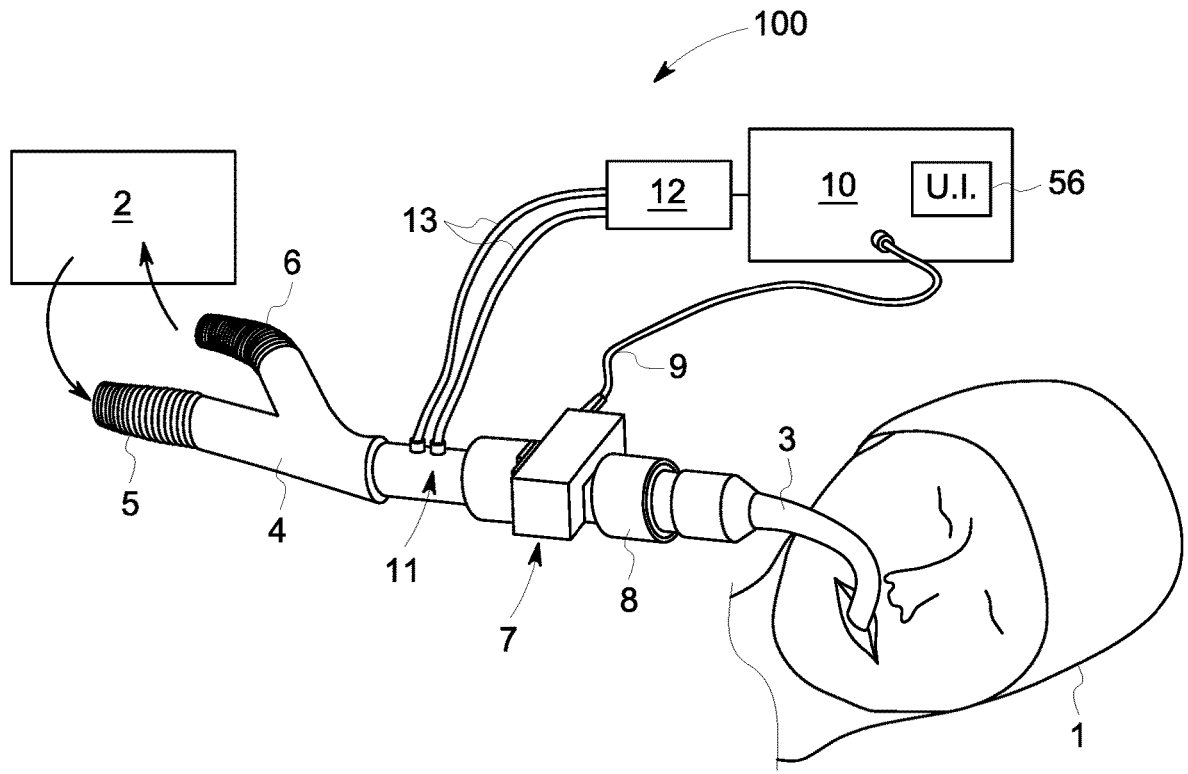
FIG. 1 illustrates a mainstream gas analyzer connected to a ventilation circuit ventilating a patient.

The inventor has recognized a need for automatic component detection for respiratory gas analyzers and has developed the disclosed system and method that utilizes color indicators and color detection to automatically identify an attached component of the gas analyzer system. For example, a mainstream gas analyzer may be configured to use color detection to automatically identify the type, or configuration, of airway adapter that gets connected to thereto. Calculation of the respiratory gas component concentration can then be performed based on the type of airway adapter identified, such as based on a zero-point value associated with the identified type of airway adapter. The color detection can also be used to authenticate a component attached to the system, such as to authenticate that an authentic airway adapter is being used rather than an uncertified or counterfeit reproduction which may not be manufactured to the same specifications as the authentic airway adapter for which the gas analyzer is calibrated.

As described above, a zero-point value must be determined for each different airway adapter configuration. The zero-point value represents the detector signal obtained at a particular measurement wavelength when none of the IR radiation at that wavelength is absorbed by the sample gas. Various airway adapter types are provided, such as patient-size dependent configurations—e.g., neonatal, pediatric, and adult airway adapters. Additionally, airway adapters may be disposable or reusable. Reusable airway adapters use high-quality plastic material for the body, where the plastic material is configured to withstand autoclaving and other harsh cleaning processes. Reusable airway adapters typically have separately-formed measurement windows comprised of a different material, such as sapphire. Disposable adapters are manufactured differently using different materials and may be manufactured using a single plastic material where the windows are made of the same material as the adapter body. Disposable adapters are not made to be washed or autoclaved and are configured for single-use applications.

Each airway adapter configuration has different IR transmittance properties, and thus each airway adapter has a different zero-point value. For example, different window properties, including different shapes and materials, will transmit IR differently. Thus, an accurate zero-point value must be determined for each type of airway adapter in order to perform accurate gas component measurements. Thus, a zero-point value must be known for each airway adapter type—e.g., neonatal reusable, neonatal disposable, pediatric reusable, pediatric disposable, adult reusable, adult disposable—prior to performing measurement using that type of airway adapter.

Different zeroing procedures are known and utilized in current gas sensor systems, which may be manual or automatic. Zeroing, or determining a zero-point value for a particular airway adapter, is a very difficult procedure to conduct during patient ventilation because it requires that no respiratory gasses are passing through the airway adapter. Thus, the airway adapter has to be zeroed outside of the patient breathing circuit. If the user forgets to set the zero-point value prior to connecting a new airway adapter to the breathing circuit of the patient, then the breathing circuit has to be disconnected to set the zero-point. Particularly in the instance of mainstream gas analyzers, disconnecting the analyzer system requires briefly stopping patient ventilation, which is detrimental to the patient and can cause negative health consequences.

Accordingly, the inventor has recognized that an automatic zeroing process is desirable which can detect and automatically determine the airway adapter configuration of a newly-connected airway adapter 8, and to access a stored zero-point value based on the identified type of airway adapter 8. Additionally, the inventor has recognized a need for automatic detection and/or recognition of other component types within the gas sensor system. For example, the inventor has recognized that automatic component identification of a sample gas line type and/or water trap type is likewise desirable and can be performed using color indication and identification, as described herein.

As exemplified in FIGS. 1-8 and variously discussed herein, the disclosed respiratory gas sensor system 100 includes a gas analyzer 7 equipped with one or more color detection systems 40 such that it performs automatic identification of one or more components attached thereto. Specifically, a color detection system 40 detects a color indicator 60 on the detected component of the system. A controller 54 is configured to proceed accordingly using information that is known based on the identified component—such as a zero-point value associated with the airway adapter type. For example, the controller 54 may be configured to calculate a respiratory gas component measurement based on information provided by the color detection system. Other control instructions may be dependent on the color information provided by the color detection system and are dependent on the system component being identified. Various examples are provided herein.

Figure 4:
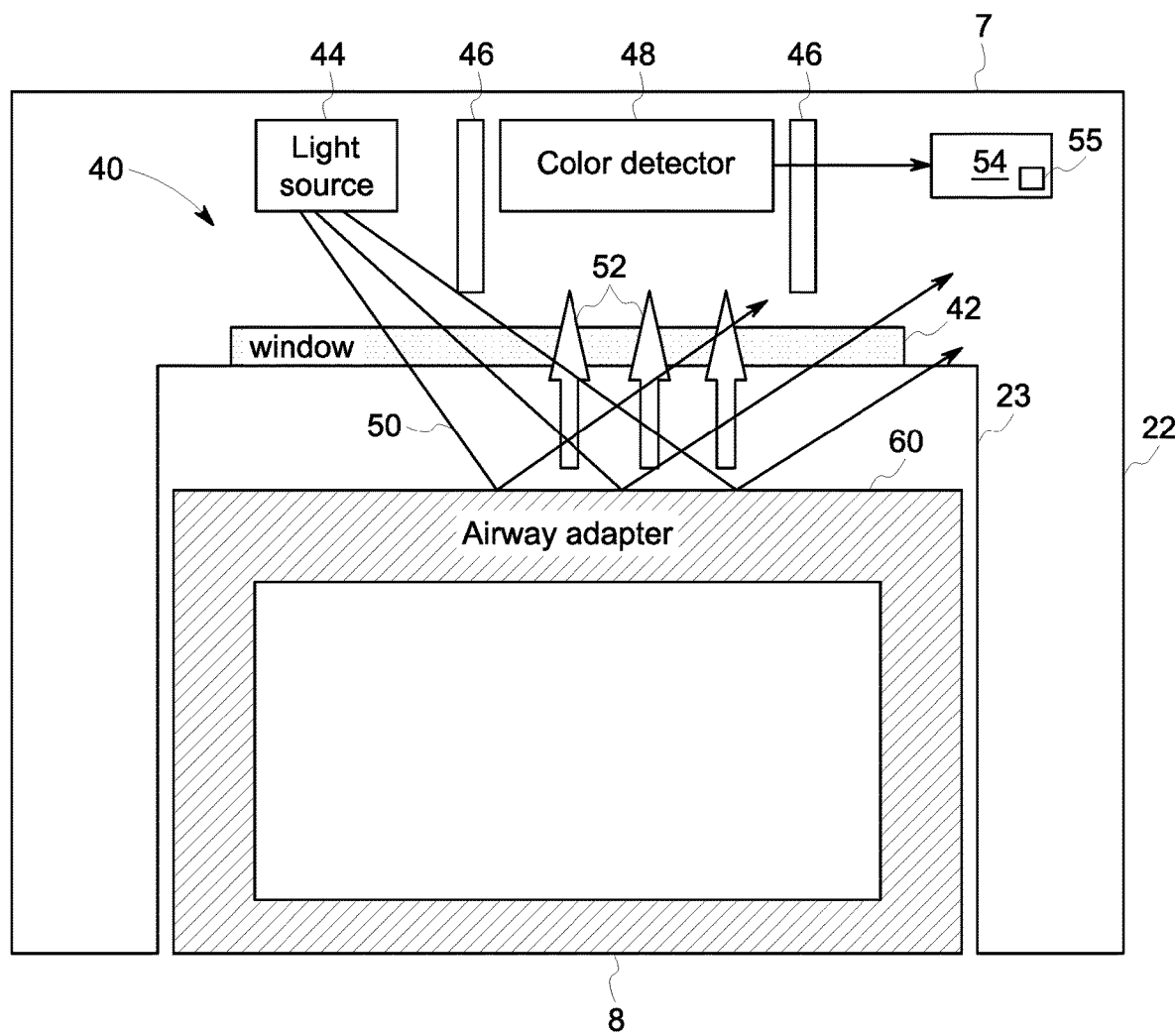
FIG. 4 depicts a cross-sectional view of a mainstream gas analyzer fitted with an airway adapter according to one embodiment of the disclosure.

As shown in FIG. 4, the color detection system 40 includes a light source 44 configured to emit light onto a color indicator 60 on the component being identified (e.g., the airways adapter 8), wherein the color indicator is one of a predefined set of colors. A color detector 48 is configured to detect light reflected by the color indicator 60 so as to identify color information. For example, the color detector 48 may be a red-green-blue (RGB) sensor, or may be another type of color sensor. The color information generated by the color detector 48 (such as RGB values) is provided to a controller 54, which is programmed to use the information in a particular way depending on the component being identified. The controller 54 accesses a table or other data structure that associates the detected color information with information relating to a relevant component or component-dependent value. The controller 54 is configured to receive color indicators for a predefined set of colors. For example, a particular color detector 48 may be associated with a particular interpretation of the identified color information—e.g., dependent on whether the color detection system 40 is positioned to read a color indicator on an airway adapter 8, on a sidestream sampling line 24, or a water trap 27. For example, a color indicator may be placed on an airway adapter 8, where each airway adapter type (e.g. neonatal reusable, neonatal disposable, pediatric reusable, pediatric disposable, adult reusable, adult disposable, etc.) has a color indicator being a predetermined one of a predefined set of colors.

A color detections system 40 is provided in the gas analyzer 7 and placed such that it can detect the color indicator 60 on the airway adapter 8. The color detection system 40 is positioned and configured to emit and detect light reflected by the color indicator 60 on the airway adapters 8 so as to identify the airway adapter type. In one embodiment, the color indicator identification can be used to set a zero-point value associated with the airway adapter configuration. Thereby, automatic determination of a zero-point value for accurately determining the respiratory gas component using that particular airway adapter can be performed. Similarly, color detection systems 40 may be incorporated in a sidestream gas analyzer in order to detect a type of sampling line and/or type of water trap based on the color information. Thereby, the type of sampling line and/or the type of water trap connected to the sidestream gas analyzer can be automatically determined, and the controller can control the gas sensor system accordingly.

Additionally, the color detection system 40 disclosed herein can be utilized to detect the presence or absence of a component to the respiratory gas sensor system, such as detecting the presence or absence of the airway adapter, the sampling line, the water trap, or any other removable component of the respiratory gas sensor system.

Referring back to FIG. 1, the examples shown will be described in greater detail. A respiratory circuit with a medical gas analyzer is shown. A patient 1 is connected to a ventilator 2 using an intubation tube 3, a Y-piece 4, an inspiratory limb 5, and an expiratory limb 6. A gas analyzer 7 which may comprise an adapter 8 is connected to the intubation tube. The gas analyzer 7 in FIG. 1 is a mainstream gas analyzer measuring gases flowing between the ventilator 2 and the patient 1 without withdrawing samples of the gas to a separate gas analyzer. In other embodiments, such as a sidestream gas analyzer, the gas analyzer is positioned at a distance from the flow between the ventilator 2 and the patient 1 (see e.g., FIGS. 6-8), and in such embodiments IR radiation is utilized for gas component measurement in largely the same way.

The analyzer shown in FIG. 1 is electrically connected via cable 9 to the patient monitor 10. The gas component measured may be carbon dioxide ($CO_2$), nitrous oxide ($N_2O$), or any of the volatile anesthetic agents—e.g., halothane, enflurane, isoflurane, desflurane, and sevoflurane. Additionally, there may be a spirometry adapter 11 for measuring the gas flow in the respiratory circuit. In this example, the sensor 12 is located at the distal end of two pressure relying tubes 13. The spirometry sensor may be separately connected as in FIG. 1 or it can be integrated into the mainstream gas analyzer, and may be similarly provided and incorporated in sidestream gas analyzers.

Figure 2:
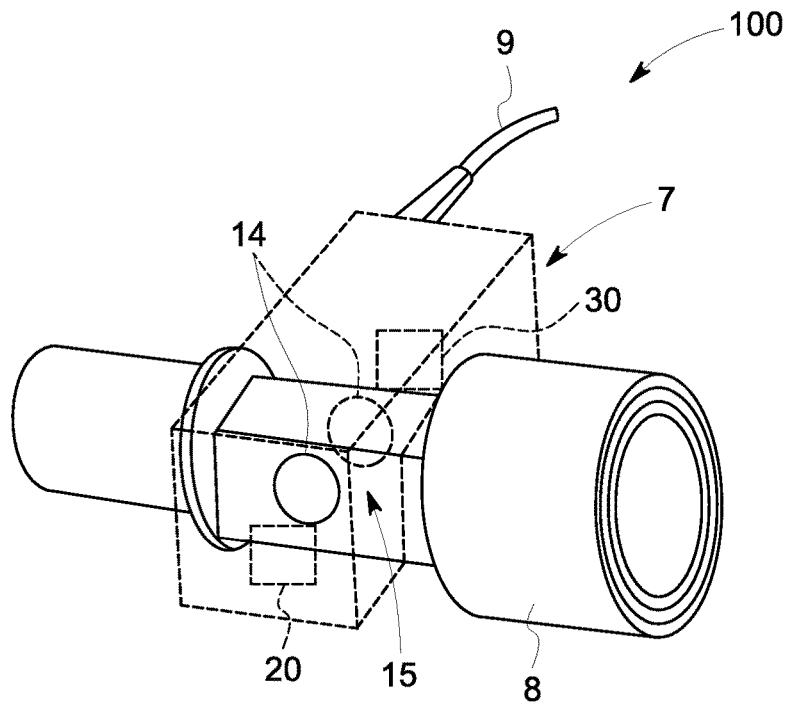
FIG. 2 shows an airway adapter and a mainstream gas analyzer connected thereto.
Figure 3:
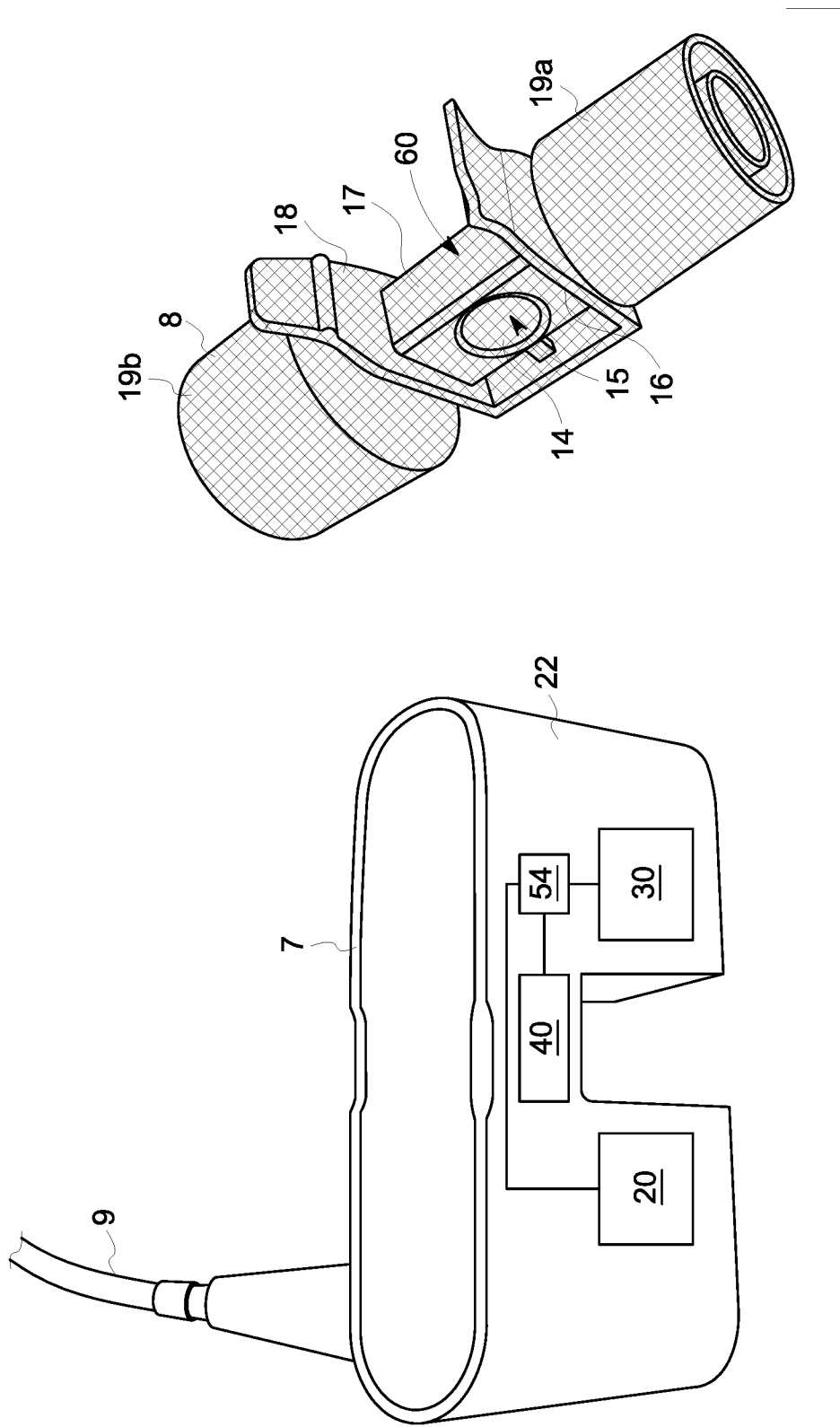
FIG. 3 shows an airway adapter and a mainstream gas analyzer, shown in a disconnected state.

In FIG. 2, a different view of the gas analyzer 7 is depicted in order to better show the components within the gas analyzer and construction of the adapter 8, which may be disposable or reusable. It is provided with at least one optical window 14 for allowing the IR radiation to be absorbed by the gas components in the measuring chamber between the optical windows. Typically there are two IR-transmitting optical windows 14. As also depicted in FIG. 3, the IR emitter 20 is located on one side of the adapter and one or more detector(s) 30 on the opposite side in such a way that the IR radiation is directed from the emitter 20, through the windows 14 and to the detector(s) 30.

The signals, or radiation measurement data, from each detector 30 gets amplified and modified to determine the concentration of the respiratory gas component to be measured. As mentioned above, the measured respiratory gas components can be any IR-absorbing component, such as carbon dioxide, nitrous oxide, or different volatile anesthetic agents. All these gases absorb IR radiation within some specific wavelength region and this region is selected (i.e., the measurement wavelength), such as using a narrowband filter, and the provided to the detector 30.

Figure 6:
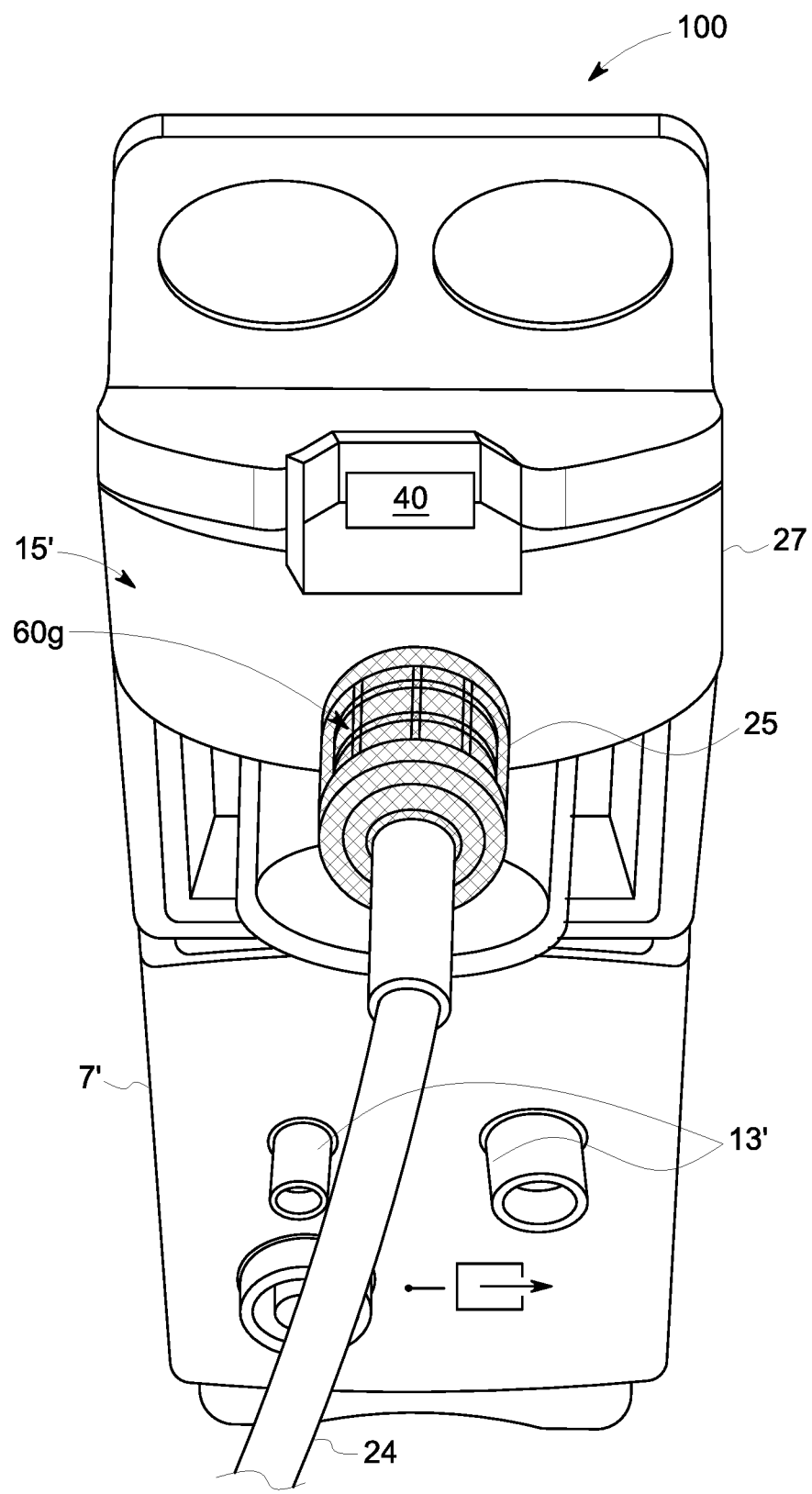
FIG. 6 depicts a medical sidestream gas analyzer according to one embodiment of the disclosure.
Figure 7:
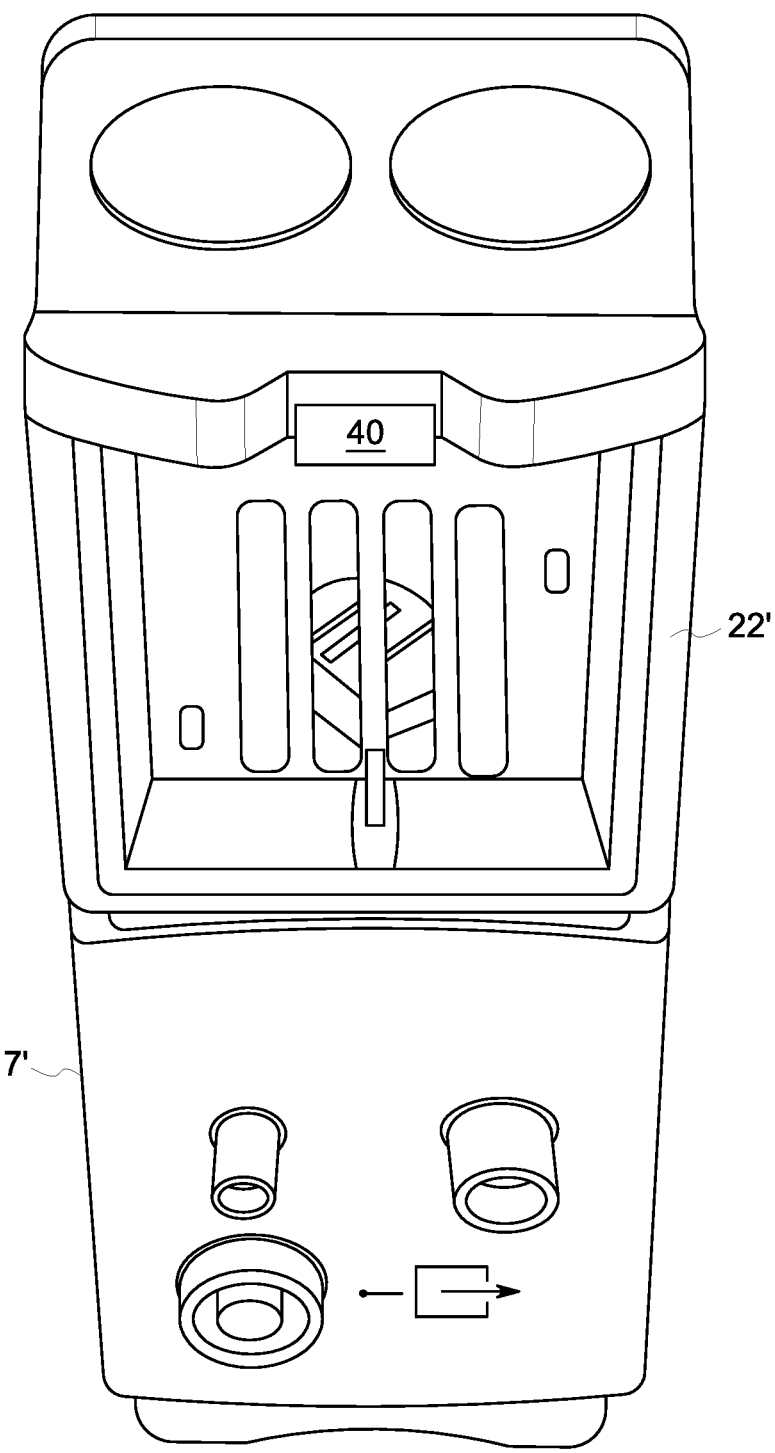
FIG. 7 depicts a medical sidestream gas analyzer according to another embodiment of the disclosure.

FIGS. 6-7 depict a sidestream gas analyzer embodiment. In the example, the sidestream gas analyzer 7' is connected to the ventilation circuit by the gas sampling line. The gas sampling line provides a gas sample from the patient's breathing circuit to the sidestream measurement chamber 15'. The sidestream gas analyzer 7' then measures gas concentrations of particular respiratory gasses, as is described herein. In the sidestream embodiment, the IR source 20 emits the IR wavelengths through the sidestream measurement chamber 15', such as via a window 14' on either side of a housing containing the measurement chamber. A detector 30 is positioned on an opposite side of the measurement chamber 15' from the IR source 20 and is configured to detect the amount of radiation transmitted therethrough, as is described herein. The measurements by the detector 30 are processed, including compared to a zero-point value, to determine the gas concentrations and such information is provided to the patient monitor 10 via cable 9.

In both the sidestream and mainstream embodiments, the radiation measurement data provided by the detector 30 is processed, including compared to a zero-point value, to determine the respiratory gas component concentration within the respective measurement chamber. Referring to FIG. 3, the gas analyzer 7 may include a controller 54 that calculates the respiratory gas component concentration based on the radiation measurement data, and may be configured to adjust the calculation methods based on information provided by one or more color detections system 40. Each color detection system 40 is configured to detect color information from a color indicator 60 on a component of the respiratory gas sensor system 100.

As described herein, different airways adapter types may be used, and each provided with a particular color indicator 60 associated with that type of airway adapter 8. As described in more detail below, the color indicator may occupy a portion of the airway adapter 8, or may be the entire exterior surface of the airway adapter 8. For example, the airway adapter 8 may be molded of a colored plastic, where each airway adapter type is molded with a different one of the predefined set of colored plastics. In the example in FIG. 3, the entire airway adapter 8 body is molded of an orange-colored plastic. The color detection system 40 is configured to reflect light off of a portion of the airway adapter 8 body so as to measure color information.

Figure 8:
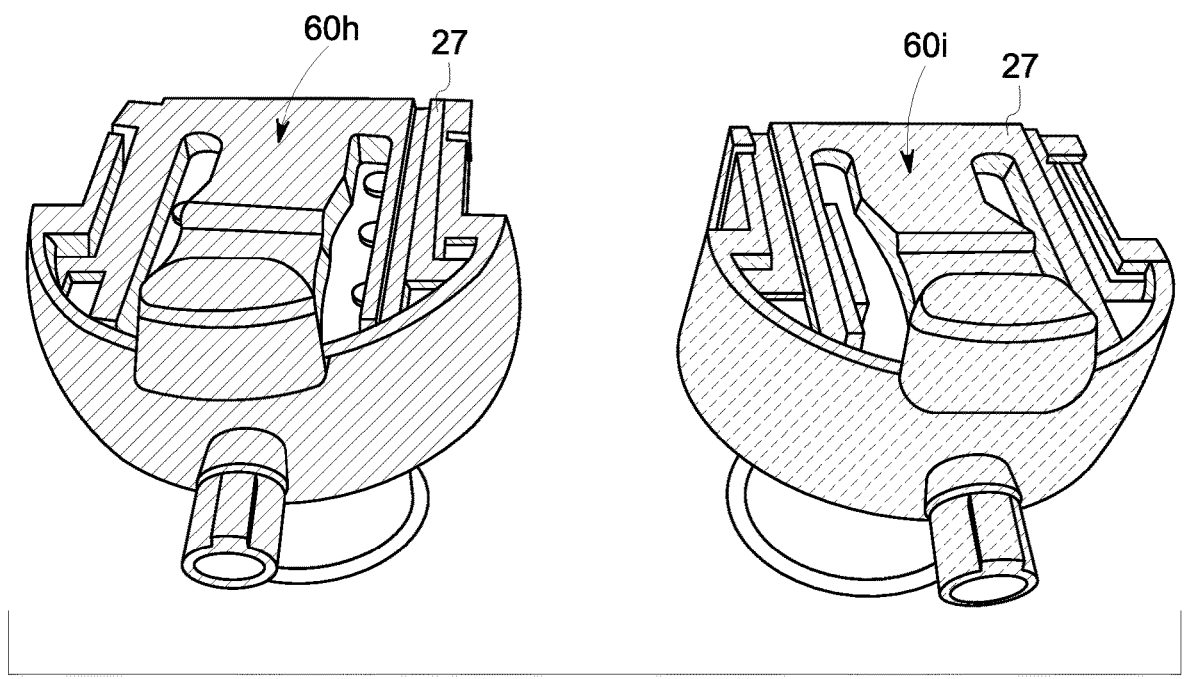
FIG. 8 depicts water traps with color indicators according to one embodiment of the disclosure.

Referring also to FIG. 4, the depicted example is arranged such that a flat top portion 17 of the airway adapter 8 above the measurement chamber 15 is utilized for the color measurement. In other embodiments, other portions of the airway adapter 8 may be utilized as the color indicator 60. For example, the vertical side portion 18 that is perpendicular to the flat top portion 17 may be utilized as the measurement surface of the color indicator. In still other embodiments, a different surface on the airway adapter 8 may be utilized, such as the exterior chamber sidewall 16, or one of the connector ends 19a, 19b. In still other embodiments, the color indicator 60 may be on a different component of the system 100, such as on a sampling line 24 or water trap 27 in a sidestream embodiment (FIGS. 6-8).

As depicted in FIG. 4, the color detection system 40 includes a light source 44 and a color detector 48. The light source 44 is configured to emit light 50 onto the color indicator 60. At least a portion of that light is reflected by the color indicator 60. The color detector 48 is positioned so that a portion of reflected light 52 from the color indicator 60 is received and measured. In one embodiment, the light source, or light emitter 44, is a light-emitting diode (LED), such as a white LED. The color detector 48 may be, for example, an RGB sensor configured to measure an amount of light that reflects from the color indicator 60. The color detector is configured to output color information indicating a dominant color in the detected light, which will be the color of the color indicator 60 (assuming that the airway adapter or other detected component is present).

In one embodiment, the color detection system 40 may include one or more dividers 46 configured to isolate the light reflected to the color detector 48 as much as possible such that the majority of the light sensed by the color detector 48 is reflected light 52 off of the color indicator 60 and not light directly received from the light emitter 44 or light reflected off of other surfaces. In the example, the divider 46 surrounds the color detector 48 and provides a barrier between the light emitter 44 and the color detector 48. In other embodiments, the divider 46 may only extend between the light emitter 44 and the detector 48.

The light emitter 44 and the color detector 48 may be positioned behind a window 42 in the housing 22 of the gas analyzer 7. The window 42 is transparent to visible light and, for example, may be comprised of polycarbonate or other clear plastic material. The window 42 protects the light emitter 44 and the color detector 48 from dirt and/or other contaminants and provides a cleanable surface. In the example at FIG. 4, the window 42 is positioned flush with a top interior surface 23 of the housing 22 of the gas analyzer 7, which is inside of the recess where the airway adapter 8 fits with the gas analyzer 7. In other embodiments, the window may be recessed from the surface 23 of the housing 22, or may protrude from the surface 23. In still other embodiments, the divider 46 between the light emitter 44 and the color detector 48 may extend further down and the window 42 may be divided such that separate windows are provided for each of the light emitter 44 and the color detector 48.

Referring to FIGS. 5A and 5B the color indicator may take different forms, and may comprise the entire body surface of the airway adapter 8, or may be on only a portion of the airway adapter body. FIG. 5A depicts three different airway adapter 8a-8c types, each having an assigned color indicator. In the depicted example, each of the airway adapters 8a-8c has a corresponding color indicator 60a-60c, where the entire airway adapter 8a-8c has a body comprised of a colored plastic that is the assigned one of the predefined set of colors that is associated with that type of airway adapter 8a-8c. In FIG. 5B, just the flat top portion 17 of each airway adapter 8d-8f has the color indicator 60d-60f. Namely, the flat top portion 17 of each of the three different airway adapter 8d-8f types has a color indicator 60d-60f being an assigned one of the predefined set of colors for the different airway adapter types 8d-8f. For example, the airway adapter bodies may be comprised of a clear plastic material, and the color indicators 60d-60f may be stickers, paint, or some other colored material applied to the flat top portion 17. In this way, the color indicator 60d-60f can be applied to the airway adapters 8d-8f after manufacture, and thus does not significantly add to the cost of manufacture. This may be particularly useful for disposable airway adapter types, where any cost increase is of particular concern. In other embodiments, the flat top portion 17 may be molded of a different plastic than the rest of the body of the airway adapter 8d-8f such that the color indicator 60d-6f is integrated into the body.

Referring again to FIG. 4, color information for each one of the predefined set of color indicators (e.g. 60a-60f) is associated with a zero-point value for the corresponding airway adapter 8a-8f. For example, a table correlating such color information with zero-point values may be stored on a storage device 55 associated with the controller 54. The storage device 55 may be, for example, memory comprising part of the controller, or may otherwise be accessible by the controller 54. The storage device may comprise any type or types of non-volatile and/or volatile memory, such as read-only memory (ROM) and random access memory (RAM).

In certain embodiments, the controller 54 may be configured to determine whether or not any airway adapter is connected to the gas analyzer. For example, the controller 54 may be configured to determine whether a threshold amount, or magnitude, of reflected light is received at the color detector 48. If insufficient light is received, it will be interpreted as indicating that the airway adapter 8 is not present, as light from the light emitter 44 is not being reflected back toward the color detector 48 from the color indicator 60.

If an insufficient magnitude of light is received and indicated by the detector 48, then the controller 54 may be configured to generate an alert and/or prohibit determination of the respiratory gas component measurement. Similarly, if the reflective light 52 received at the color detector 48 is not indicative of one of the predefined set of colors, then the controller 54 may be configured to generate a corresponding alert. For example, if the color information does not match with the stored color information for one of the predefined set of colors then the controller 54 may generate an alert via the user interface 56 on the patient monitor 10. Alternatively or additionally, the controller may be configured such as it does not determine any respiratory gas component measurement unless the color detector matches the color information for one of the predefined set of colors. Where the color information is utilized to identify a zero-point value for the airway adapter, for example, the determination of the respiratory gas component concentration may be prohibited because no zero-point value will be available if the color information does not match up with one of the predefined set of colors.

FIGS. 6-8 depict a side stream gas analyzer 7' having one or more color indicators 60g-60i. In the example of FIG. 6, the color indicator 60g is on a sampling line connector 25, and wherein the color detection system 40 is configured to detect light reflected by the color indicator 60g on the sampling line connector 25. Thereby, the controller 54, in cooperation with the color detector 48, may determine the type of sampling line 24 based on the reflected light 52 that reflects off the color indicator 60g on the sampling line 24. The identification of the sampling line type may be utilized by the controller 54 to set values used in calculating the gas component measurement, as well as to dictate operation of the pump associated with the sidestream system. It is important to detect the sampling line type because sampling line material and the inside diameter of the sampling line have impact on the gas measurement performance. Sampling line length may also be utilized when calculating values that are dependent on the sampling delay, which is caused by the sampling line length and inside diameter. Further, the controller 54 may be configured to determine whether any sampling line is connected. If gas measurement system notices that no sampling line is connected, it may be configured to stop the pump because the pump is a wearing component and stopping it extends the lifetime of the pump. The controller 54 may further be configured to, upon determination that no gas sampling line is attached to the sidestream detector, stop or limit other functions inside system as well to save power and/or extend lifetime of the wearing components.

Alternatively or additionally, the color indicator may be on a water trap 27 that fits with the sidestream gas analyzer 7'. In such embodiment, the color detection system 40 may be positioned in the sidestream gas analyzer 7' so as to measure reflected light off a portion of the water trap 27. FIG. 7 depicts on such embodiment, where the color detection system 40 is positioned within the housing 22' of the sidestream gas analyzer 7' at a location above the connection area for the water trap 27, which may be an arrangement like that depicted in FIG. 4. Thereby, the color detection system 40 is positioned to detect color information of a connected water trap 27 and/or to detect the presence or absence of the water trap based on the amount of reflected light received at the color detector 48 as is described above. FIG. 8 depicts examples of water traps 27 having color indicators 60h and 60i, where each of the color indicators 60h and 60i are associated with a water trap configuration. For example, the water trap may be designed for specific use because conditions in the operating room and the intensive care unit differ significantly between each other. The gases are different in the operating room and treatments are typically short. In the intensive care unit, the treatments are long and much more water and different liquids accumulate inside breathing circuit. The water trap is also an efficient air filter, which protects the pneumatics of the gas measurement device so it is important to detect the presence of the water trap and if, it is not present, stop the pump and and/or limit other functions to save power and/or extend lifetime of wearing components.

In various embodiments the color indicator may be a portion or the entirety of the water trap 27 being comprised of a colored molded plastic. In other embodiments, the color indicator 60h and 60i may be a sticker, paint, or some other color treatment applied to the surface of the water trap 27 or some portion thereof.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

I claim:

1. A gas analyzer for measuring a respiratory gas component, the gas analyzer comprising:
   an emitter that transmits infrared (IR) radiation through a measurement chamber containing respiration gas;
   at least one IR detector configured to receive at least a portion of the IR radiation transmitted through the measurement chamber and to generate radiation measurement data;
   a light source separate from the emitter configured to emit light onto a color indicator, wherein the color indicator is one of a predefined set of colors;
   a color detector separate from the IR detector configured to detect light reflected by the color indicator so as to identify color information; and
   a controller configured to determine a respiratory gas component concentration within the measurement chamber based on the color information and the radiation measurement data.

2. The gas analyzer of claim 1, wherein the gas analyzer is a maintstream gas analyzer and the color indicator is on an airway adapter fitted to the maintstream gas analyzer, wherein the controller is configured to identify a zero-point value for determining the respiratory gas component measurement based on the color information.

3. The gas analyzer of claim 2, further comprising:
   a storage device storing a table correlating color information for each of the predefined set of colors with a respective zero-point value; and
   wherein the controller is configured to access the table to identify the zero-point value based on the color information.

4. The gas analyzer of claim 3, wherein the controller is further configured to detect presence or absence of the airway adapter based on the color information and to prohibit the determination of the respiratory gas component measurement if the airway adapter is absent.

5. The gas analyzer of claim 2, wherein the color indicator is on an exterior surface of the airway adapter.

6. The gas analyzer of claim 5, wherein the color indicator is on a flat top portion of the airway adapter above the measurement chamber, and wherein the light source and the color detector are positioned adjacent to one another in the gas analyzer so as to measure the color information from the color indicator.

7. The gas analyzer of claim 1, further comprising a window on a housing of the gas analyzer, wherein the light source is positioned to emit the light through the window onto the color indicator, and the color detector is positioned to receive the light reflected by the color indicator through the window.

8. The gas analyzer of claim 1, further comprising:
   a storage device storing a table containing color information for each of the predefined set of colors; and
   wherein the controller is further configured to determine whether the color information from the color detector matches the color information for one of the predefined set of colors prior to determining the respiratory gas component measurement.

9. The gas analyzer of claim 8, wherein the controller is further configured to generate an alert if the color information from the color detector does not match the color information for any of the predefined set of colors.

10. The gas analyzer of claim 8, wherein the controller is further configured to prohibit the determination of the respiratory gas component measurement if the color information from the color detector does not match the color information for any of the predefined set of colors.

11. The gas analyzer of claim 1, wherein the gas analyzer is a sidestream gas analyzer and the color indicator is on a sampling line connector, wherein the controller is configured to determine a sampling line type based on the color information and/or to detect presence or absence of the sampling line based on the color information and to prohibit the determination of the respiratory gas component concentration if the sampling line is absent.

12. The gas analyzer of claim 1, wherein the gas analyzer is a sidestream gas analyzer and the color indicator is on a water trap, wherein the controller is configured to determine a water trap type based on the color information.

13. The gas analyzer of claim 12, wherein the controller is further configured to detect presence or absence of the water trap based on the color information and to prohibit the determination of the respiratory gas component concentration if the water trap is absent.

14. A respiratory gas sensor system for measuring a respiratory gas component, the respiratory gas sensor system comprising:
   an airway adapter providing a measurement chamber for respiratory gases, wherein the airway adapter includes a color indicator that is one of a predefined set of colors;
   a gas analyzer configured to fit with the airway adapter and measure a respiratory gas component concentration in the measurement chamber, the gas analyzer including:
   a light source configured to emit light onto the color indicator, wherein the light source is separate from an emitter used to measure the respiratory gas component in the measurement chamber;
   a color detector configured to detect light reflected by the color indicator so as to identify color information, wherein the color detector is separate from a detector used to generate radiation measurement data regarding the respiratory gas component in the measurement chamber; and
   a controller configured to automatically identify a zero-point value based on the color information, and then to utilize the zero-point value to determine the respiratory gas component concentration.

15. The respiratory gas sensor system of claim 14, further comprising a storage device storing a table correlating color information for each of the predefined set of colors with a respective zero-point value; and wherein the controller is configured to access the table to identify the zero-point value based on the color information.

16. The respiratory gas sensor system of claim 15, wherein the controller is further configured to:
   determine whether the color information from the color detector matches the color information for one of the predefined set of colors prior to determining the respiratory gas component concentration; and
   generate an alert if the color information from the color detector does not match the color information for any of the predefined set of colors.

17. The respiratory gas sensor system of claim 14, wherein the controller is further configured to detect presence or absence of the airway adapter based on the color information and to prohibit the determination of the respiratory gas component concentration if the airway adapter is absent.

18. The respiratory gas sensor system of claim 14, wherein the color indicator is on a flat top portion of the airway adapter above the measurement chamber, and wherein the light source and the color detector are positioned adjacent to one another in the gas analyzer so as to measure the color information from the flat top portion.

19. The respiratory gas sensor system of claim 14, wherein the airway adapter is comprised of a molded plastic that is one of the predefined set of colors.

20. The respiratory gas sensor system of claim 14, further comprising a window on a housing of the gas analyzer, wherein the light source is positioned to emit the light through the window onto the color indicator, and the color detector is positioned to receive the light reflected by the color indicator through the window.

* * * * *